(12) United States Patent
Chen et al.

(10) Patent No.: US 9,173,583 B2
(45) Date of Patent: Nov. 3, 2015

(54) NEURAL SENSING DEVICE AND METHOD FOR MAKING THE SAME

(71) Applicant: Advanced Semiconductor Engineering, Inc., Kaohsiung (TW)

(72) Inventors: Kuo-Hua Chen, Kaohsiung (TW); Chih-Wei Chang, Yangmei (TW); Jin-Chern Chiou, Hsinchu (TW)

(73) Assignee: Advanced Semiconductor Engineering, Inc. (TW)

( * ) Notice: Subject to any disclaimer, the term of this patent is extended or adjusted under 35 U.S.C. 154(b) by 0 days.

(21) Appl. No.: 13/840,817

(22) Filed: Mar. 15, 2013

(65) Prior Publication Data

US 2014/0275929 A1    Sep. 18, 2014

(51) Int. Cl.
| | |
|---|---|
| *A61B 5/0478* | (2006.01) |
| *A61B 5/00* | (2006.01) |
| *A61B 5/04* | (2006.01) |
| *A61B 5/0492* | (2006.01) |
| *H01L 23/48* | (2006.01) |
| *A61B 5/0496* | (2006.01) |
| *A61N 1/05* | (2006.01) |

(52) U.S. Cl.
CPC ........... *A61B 5/0478* (2013.01); *A61B 5/04001* (2013.01); *A61B 5/0492* (2013.01); *A61B 5/6868* (2013.01); *H01L 23/481* (2013.01); *A61B 5/0496* (2013.01); *A61B 2562/028* (2013.01); *A61B 2562/043* (2013.01); *A61N 1/0529* (2013.01)

(58) Field of Classification Search
CPC .. A61B 5/04001; A61B 5/0478; A61B 5/685; A61B 5/6868; A61B 2562/046
USPC ............................ 600/373, 377, 378; 607/116
See application file for complete search history.

(56) References Cited

U.S. PATENT DOCUMENTS

| | | | |
|---|---|---|---|
| 3,761,782 A | | 9/1973 | Youmans |
| 4,394,712 A | | 7/1983 | Anthony |
| 4,499,655 A | | 2/1985 | Anthony |
| 4,807,021 A | | 2/1989 | Okumura |
| 4,842,699 A | | 6/1989 | Hua et al. |
| 4,897,708 A | | 1/1990 | Clements |
| 4,969,468 A | * | 11/1990 | Byers et al. .................... 600/373 |
| 4,982,265 A | | 1/1991 | Watanabe et al. |
| 5,166,097 A | | 11/1992 | Tanielian |
| 5,191,405 A | | 3/1993 | Tomita et al. |
| 5,215,088 A | * | 6/1993 | Normann et al. ............. 600/377 |
| 5,229,647 A | | 7/1993 | Gnadinger |
| 5,239,448 A | | 8/1993 | Perkins et al. |

(Continued)

FOREIGN PATENT DOCUMENTS

| | | |
|---|---|---|
| JP | 2002246540 A | 8/2002 |
| JP | 2004228135 A | 8/2004 |
| TW | 200612539 A | 4/2006 |

*Primary Examiner* — Lee S Cohen
(74) *Attorney, Agent, or Firm* — Morgan Law Offices, PLC

(57) ABSTRACT

The present invention provides a neural sensing device and method for making the same. The neural sensing device includes a base, an integrated circuit portion, a plurality of microprobes and at least one conductive via. The base has an active surface and a backside surface. The integrated circuit portion is disposed on the active surface of the base. The microprobes protrude from the backside surface of the base. The through silicon via is disposed in the base and electrically connects the integrated circuit portion and the microprobes. Each of the microprobes includes an isolation layer partially covering a conductive layer.

19 Claims, 12 Drawing Sheets

(56) References Cited

U.S. PATENT DOCUMENTS

| | | |
|---|---|---|
| 5,308,443 A | 5/1994 | Sugihara |
| 5,404,044 A | 4/1995 | Booth et al. |
| 5,615,477 A | 4/1997 | Sweitzer |
| 5,643,831 A | 7/1997 | Ochiai et al. |
| 5,969,238 A | 10/1999 | Fischer |
| 5,998,292 A | 12/1999 | Black et al. |
| 6,276,599 B1 | 8/2001 | Ogawa |
| 6,329,631 B1 | 12/2001 | Yueh |
| 6,406,934 B1 | 6/2002 | Glenn et al. |
| 6,448,506 B1 | 9/2002 | Glenn et al. |
| 6,457,633 B1 | 10/2002 | Takashima et al. |
| 6,511,463 B1 * | 1/2003 | Wood et al. .................. 604/272 |
| 6,577,013 B1 | 6/2003 | Glenn et al. |
| 6,670,269 B2 | 12/2003 | Mashino |
| 6,699,787 B2 | 3/2004 | Mashino |
| 6,740,950 B2 | 5/2004 | Paek |
| 6,812,549 B2 | 11/2004 | Umetsu et al. |
| 6,815,348 B2 | 11/2004 | Mashino |
| 6,962,829 B2 | 11/2005 | Glenn et al. |
| 7,078,269 B2 | 7/2006 | Yamasaki et al. |
| 7,134,198 B2 | 11/2006 | Nakatani |
| 7,157,372 B1 | 1/2007 | Trezza |
| 7,215,032 B2 | 5/2007 | Trezza |
| 7,222,420 B2 | 5/2007 | Moriizumi |
| 7,238,590 B2 | 7/2007 | Yang et al. |
| 7,262,475 B2 | 8/2007 | Kwon et al. |
| 7,276,787 B2 | 10/2007 | Edelstein et al. |
| 7,285,434 B2 | 10/2007 | Yee et al. |
| 7,298,030 B2 | 11/2007 | McWilliams et al. |
| 7,334,326 B1 | 2/2008 | Huemoeller et al. |
| 7,365,436 B2 | 4/2008 | Yamano |
| 7,368,305 B2 | 5/2008 | van der Weide et al. |
| 7,371,602 B2 | 5/2008 | Yee |
| 7,388,293 B2 | 6/2008 | Fukase et al. |
| 7,415,762 B2 | 8/2008 | Fukase et al. |
| 7,429,333 B2 | 9/2008 | Chiou et al. |
| 7,482,272 B2 | 1/2009 | Trezza |
| 7,508,057 B2 | 3/2009 | Shiraishi et al. |
| 7,508,079 B2 | 3/2009 | Higashi |
| 7,528,053 B2 | 5/2009 | Huang et al. |
| 7,538,033 B2 | 5/2009 | Trezza |
| 7,553,752 B2 | 6/2009 | Kuan et al. |
| 7,560,744 B2 | 7/2009 | Hsiao et al. |
| 7,598,163 B2 | 10/2009 | Callahan et al. |
| 7,605,463 B2 | 10/2009 | Sunohara |
| 7,625,818 B2 | 12/2009 | Wang |
| 7,642,132 B2 | 1/2010 | Huang et al. |
| 7,656,023 B2 | 2/2010 | Sunohara et al. |
| 7,659,202 B2 | 2/2010 | Trezza |
| 7,666,711 B2 | 2/2010 | Pagaila et al. |
| 7,678,685 B2 | 3/2010 | Sunohara et al. |
| 7,681,779 B2 | 3/2010 | Yang |
| 7,687,397 B2 | 3/2010 | Trezza |
| 7,691,747 B2 | 4/2010 | Lin et al. |
| 7,733,661 B2 | 6/2010 | Kossives et al. |
| 7,741,148 B1 | 6/2010 | Marimuthu et al. |
| 7,741,152 B2 | 6/2010 | Huang et al. |
| 7,741,156 B2 | 6/2010 | Pagaila et al. |
| 7,772,081 B2 | 8/2010 | Lin et al. |
| 7,772,118 B2 | 8/2010 | Yamano |
| 7,786,008 B2 | 8/2010 | Do et al. |
| 7,786,592 B2 | 8/2010 | Trezza |
| 7,795,140 B2 | 9/2010 | Taguchi et al. |
| 7,808,060 B2 | 10/2010 | Hsiao |
| 7,808,111 B2 | 10/2010 | Trezza |
| 7,811,858 B2 | 10/2010 | Wang et al. |
| 7,816,265 B2 | 10/2010 | Wang |
| 7,842,597 B2 | 11/2010 | Tsai |
| 7,875,479 B2 | 1/2011 | Chiou et al. |
| 7,941,201 B2 * | 5/2011 | Chiou et al. .................. 600/373 |
| 7,991,475 B1 * | 8/2011 | Tang et al. .................... 607/45 |
| 8,639,312 B2 * | 1/2014 | Clark et al. .................... 600/378 |
| 2002/0017855 A1 | 2/2002 | Cooper et al. |
| 2002/0094605 A1 | 7/2002 | Pai et al. |
| 2004/0006264 A1 * | 1/2004 | Mojarradi et al. ............ 600/378 |
| 2004/0054393 A1 * | 3/2004 | Stemme et al. ............... 607/149 |
| 2004/0124518 A1 | 7/2004 | Karnezos |
| 2004/0259292 A1 | 12/2004 | Beyne et al. |
| 2005/0189635 A1 | 9/2005 | Humpston et al. |
| 2005/0258545 A1 | 11/2005 | Kwon |
| 2006/0027632 A1 | 2/2006 | Akram |
| 2006/0197216 A1 | 9/2006 | Yee |
| 2007/0048896 A1 | 3/2007 | Andry et al. |
| 2007/0138562 A1 | 6/2007 | Trezza |
| 2007/0187711 A1 | 8/2007 | Hsiao et al. |
| 2008/0272486 A1 | 11/2008 | Wang et al. |
| 2009/0032928 A1 | 2/2009 | Chiang et al. |
| 2009/0039527 A1 | 2/2009 | Chan et al. |
| 2009/0140436 A1 | 6/2009 | Wang |
| 2009/0146297 A1 | 6/2009 | Badakere et al. |
| 2009/0166785 A1 | 7/2009 | Camacho et al. |
| 2009/0243045 A1 | 10/2009 | Pagaila et al. |
| 2009/0294959 A1 | 12/2009 | Chiang et al. |
| 2009/0302435 A1 | 12/2009 | Pagaila et al. |
| 2009/0302437 A1 | 12/2009 | Kim et al. |
| 2009/0309235 A1 | 12/2009 | Suthiwongsunthorn et al. |
| 2009/0321916 A1 | 12/2009 | Wang et al. |
| 2010/0059855 A1 | 3/2010 | Lin et al. |
| 2010/0065948 A1 | 3/2010 | Bae et al. |
| 2010/0133704 A1 | 6/2010 | Marimuthu et al. |
| 2010/0140737 A1 | 6/2010 | Lin et al. |
| 2010/0140751 A1 | 6/2010 | Tay et al. |
| 2010/0140752 A1 | 6/2010 | Marimuthu et al. |
| 2010/0140776 A1 | 6/2010 | Trezza |
| 2010/0148316 A1 | 6/2010 | Kim et al. |
| 2010/0187681 A1 | 7/2010 | Chen et al. |
| 2010/0197134 A1 | 8/2010 | Trezza |
| 2010/0230759 A1 | 9/2010 | Yang et al. |
| 2010/0230760 A1 | 9/2010 | Hung |
| 2010/0230788 A1 | 9/2010 | Peng |
| 2010/0244244 A1 | 9/2010 | Yang |
| 2010/0276690 A1 | 11/2010 | Chen |
| 2010/0327465 A1 | 12/2010 | Shen et al. |
| 2011/0048788 A1 | 3/2011 | Wang et al. |
| 2011/0068437 A1 | 3/2011 | Chiu et al. |
| 2014/0275911 A1 * | 9/2014 | Chen ............................ 600/372 |

* cited by examiner

NEURAL SENSING DEVICE AND METHOD FOR MAKING THE SAME

BACKGROUND OF THE INVENTION

1. Field of the Invention

The present invention relates to neurological diagnostic and therapeutic medical devices, and, more particularly, to a neural sensing device with a plurality of microprobes useful for collecting bio-electrical signals and a method for making the same.

2. Description of the Related Art

Conventional neural sensing devices for use in recording and measuring electrical activity of the brain, such as those used in electroencephalography (EEG), include a plurality of microprobes, each having a metal needle or a needle coated with a metal layer. The microprobes are utilized to penetrate the skin of the scalp to collect bio-electrical signals from a patient.

Skin is a layered structure, including two primary layers: the epidermis, which provides waterproofing and serves as a barrier to infection; and the dermis, which serves as a location for the appendages of the skin. The epidermis can be roughly divided into another two layers: the stratum corneum and the stratum germinativum. The stratum corneum includes dead skin cells, and, therefore serves as a waterproof barrier layer. The stratum germinativum comprises living cells and provides good electrical conductivity. Unfortunately, conventional neural sensing devices tend to be affected by undesired noise through the portions of the microprobes in the stratum corneum.

SUMMARY OF THE INVENTION

One aspect of the disclosure relates to a neural sensing device. In one embodiment, the neural sensing device includes a base having an active surface and a backside surface; an integrated circuit portion disposed on the active surface of the base; and a plurality of microprobes disposed on the backside surface of the base, each of the microprobes comprising: a probe body protruding from the backside surface of the base and including a tip at a distal end; a first isolation layer covering the probe body; a conductive layer covering the first isolation layer and electrically connected to the integrated circuit portion; and a second isolation layer covering the conductive layer and having an opening to expose the conductive layer around a portion of the tip. The neural sensing device can further include a conductive via disposed in the base and electrically connected to the integrated circuit portion and the conductive layer, providing a short transmission path. In an embodiment, the integrated circuit portion comprises a plurality of electrical elements, a plurality of metal layers and at least one dielectric layer, the electrical elements disposed adjacent to the active surface of the base and covered by the dielectric layer, and the metal layers embedded in the dielectric layer. In an embodiment, the probe body of each of the microprobes is formed from the base and is made of the same material, such as silicon. The materials of the first isolation layer and the second isolation layer are electrically isolative (insulative). In an embodiment, the exposed portion of the conductive layer around the tip is about 30 to 70 μm in length, so as to allow contact mostly or substantially entirely with the stratum germinativum. The neural sensing device can further include at least one redistribution layer disposed on and electrically connected to the integrated circuit portion; at least one protection layer covering the redistribution layer; and at least one under bump metallurgy (UBM) disposed on the protection layer and electrically connected to the redistribution layer. In an embodiment, the probe body of each of the microprobes has a main portion and the tip, the main portion connected to the base and the tip, the diameter of the portion of the main portion connected to the base having a diameter greater than the portion of the main portion connected to the tip.

Another aspect of the disclosure relates to a method of making a neural sensing device. In one embodiment, a method for making a neural sensing device comprises the steps of: (a) providing a wafer having a base and an integrated circuit portion disposed on an active surface of the base; (b) forming at least one through silicon via on the active surface of the base; (c) selectively removing the base from a backside surface thereof to form a plurality of probe bodies and expose the conductive via; (d) forming a first isolation layer on the probe bodies and the backside surface of the base, wherein the first isolation layer has an opening to expose the conductive via; (e) forming a conductive layer on the first isolation layer to contact the conductive via; and (f) forming a second isolation layer on the conductive layer, wherein the second isolation layer has an opening to expose a part of the conductive layer. In an embodiment, in step (b), the through silicon via further penetrates through the integrated circuit portion. Step (b) can further include the steps of: (b1) forming at least one base hole on the active surface of the base; (b2) forming a circular insulation material on a sidewall of the base hole so as to define a central groove; and (b3) filling an interconnection metal in the central groove. Step (c) can further include a step of removing a part of the circular insulation material as to expose the interconnection metal from the backside surface of the base; and in step (e), the conductive layer can contact the interconnection metal of the conductive via. Furthermore, after step (b) the method can further include (b1) forming at least one redistribution layer on the integrated circuit portion; (b2) forming at least one protection layer to cover the redistribution layer; and (b3) forming at least one under bump metallurgy (UBM) on the protection layer to electrically connect the redistribution layer. Finally, the wafer is diced to form a plurality of the neural sensing devices.

BRIEF DESCRIPTION OF THE DRAWINGS

Common reference numerals are used throughout the drawings and the detailed description to indicate the same elements. The present invention will be more apparent from the following detailed description taken in conjunction with the accompanying drawings.

DETAILED DESCRIPTION OF THE INVENTION

Figure 1:
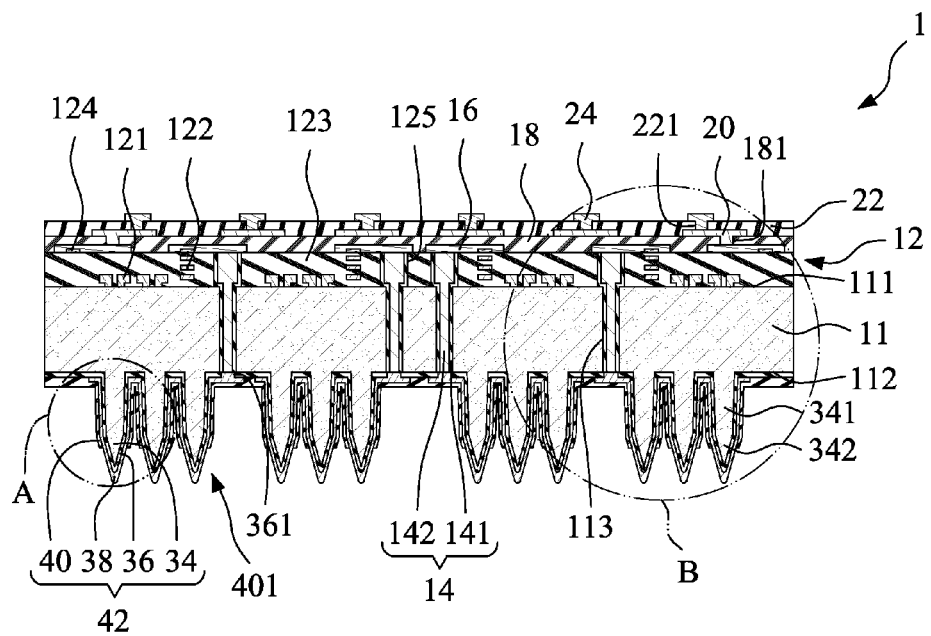
FIG. 1 illustrates a cross sectional view of a neural sensing device according to an embodiment of the present invention.

Referring to FIG. 1, a cross sectional view of a neural sensing device 1, according to an embodiment of the present invention, is illustrated. The neural sensing device 1 comprises a base 11, an integrated circuit portion 12, at least one through silicon via 14, a first redistribution layer 16, a first protection layer 18, a second redistribution layer 20, a second protection layer 22, at least one under bump metallurgy (UBM) 24 and a plurality of microprobes 42.

The base 11 has an active surface 111, a backside surface 112 and a base hole 113. In this embodiment, the material of the base 11 is silicon, and the base hole 113 is a through hole.

The integrated circuit portion 12 is disposed on the active surface 111 of the base 11. In this embodiment, the integrated circuit portion 12 comprises a plurality of electrical elements 121, a plurality of metal layers 122, at least one dielectric layer 123, at least one pad 124 and at least one upper blind hole 125. The electrical elements 121 (which can include complementary metal-oxide-semiconductor (CMOS), micro-electro-mechanical systems (MEMS), simulators, controllers, radio frequency (RF) telemetry, power receiving coil or an antenna, etc.) are disposed adjacent to the active surface 111 of the base 11 and covered by the at least one dielectric layer 123. The metal layers 122 are covered by, and embedded in, the dielectric layer 123. Usually, the integrated circuit portion 12 includes at least three metal layers 122. The pad 124 and the upmost layer of the metal layers 122 are not covered by the dielectric layer 123. In this embodiment, the thickness of the base 11 is about 200 μm and the thickness of the integrated circuit portion 12 is about 18 μm. The upper blind hole 125 penetrates through the integrated circuit portion 12. The base hole 113 communicates with the upper blind hole 125.

The through silicon via 14 is disposed in the base hole 113 and the upper blind hole 125 to electrically connect the integrated circuit portion 12 and the microprobes 42. That is, the through silicon via 14 penetrates through the base 11 and the integrated circuit portion 12. In this embodiment, the through silicon via 14 has a circular insulation material 141 and an interconnection metal 142. The circular insulation material 141 is disposed on the sidewall of the base hole 113 and the side wall of the upper blind hole 125, and defines a central groove. The interconnection metal 142 is disposed in the central groove. In this embodiment, the material of the circular insulation material 141 is polyimide (PI), the material of the interconnection metal 142 is copper (Cu), and the bottom end of the interconnection metal 142 is exposed from the backside surface 112 of the base 11.

The first redistribution layer 16 is disposed on the integrated circuit portion 12 to electrically connect the pad 124, the upmost layer of the metal layers 122 and the through silicon via 14. The first protection layer 18 is disposed on the integrated circuit portion 12 to cover the first redistribution layer 16, wherein the first protection layer 18 has at least one opening 181 to expose a part of the first redistribution layer 16. The second redistribution layer 20 is disposed on the first protection layer 18 and in the opening 181 to electrically connect the first redistribution layer 16. The second protection layer 22 is disposed on the first protection layer 18 to cover the second redistribution layer 20, wherein the second protection layer 22 has at least one opening 221 to expose a part of the second redistribution layer 20. The under bump metallurgy (UBM) 24 is disposed on the second protection layer 22 and in the opening 221 to electrically connect the second redistribution layer 20.

The microprobes 42 protrude from the backside surface 112 of the base 11. Each of the microprobes 42 comprises a probe body 34, a first isolation layer 36, a conductive layer 38 and a second isolation layer 40. The probe body 34 protrudes from the backside surface 112 of the base 11. In this embodiment, the probe body 34 is formed from the base 11. Thus, the material of the probe body 34 is silicon. The first isolation layer 36 covers, and electrically insulates, the probe body 34 and the backside surface 112 of the base 11, and has an opening 361 to expose the bottom end of the interconnection metal 142 of the through silicon via 14. The conductive layer 38 covers the first isolation layer 36. In this embodiment, the conductive layer 38 is formed on the first isolation layer 36 disposed on the probe bodies 34 and also formed on the interconnection metal 142 of the through silicon via 14, so as to contact the interconnection metal 142 of the through silicon via 14.

The second isolation layer covers the conductive layer 38 and the first isolation layer 36, and has an opening 401 to expose the tip of the conductive layer 38. The covered portion of the conductive layer 38 is electrically isolated by the second isolation layer 40 while the exposed tip of the conductive layer is not. In this embodiment, the material of the first isolation layer 36 and the second isolation layer 40 is Parylene, and the thickness of the first isolation layer 36 and the second isolation layer 40 is about 1 to 2 μm respectively. However, the material and the thickness of the second isolation layer 40 may be different from that of the first isolation layer 36. In the present embodiment, the material of the conductive layer 38 is platinum, and the thickness of the conductive layer 38 is about 450 nm.

Figure 2:
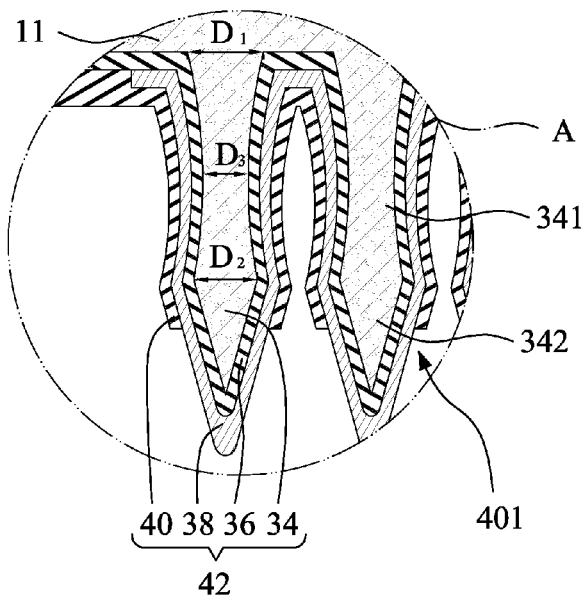
FIG. 2 illustrates a partially enlarged view of area A of FIG. 1.

Referring to FIG. 2, a partially enlarged view of area A of FIG. 1 is illustrated. The probe body 34 has a main portion 341 and a tip portion 342 and the material of the probe body 34 is silicon. The part that the main portion 341 connects with the base 11 is defined as the first part, and the part that the main portion connects the tip portion 342 is defined as the second part. The diameter $D_1$ of the first part is greater than the diameter $D_2$ of the second part. In this embodiment, $D_1$ is about 1.1 to 5 times that of $D_2$ due to the etching process used. Furthermore, if the diameter $D_2$ is slightly smaller than the diameter $D_1$, the shear stress will be easier to release from the main portion 341 to the tip portion 342. Therefore, it is easier to penetrate through the stratum corneum (SC) into the stratum germinativum (SG) to collect bio-electrical signals. In addition, since the diameter $D_1$ is greater than the diameter $D_2$, the probe body 34 is relatively firm and will not break easily. The narrowest part of the main portion 341 is defined as the third part, and the diameter $D_3$ of the third part is smaller than the diameter $D_2$ of the second part. In this embodiment, $D_3$ is about 0.5 to 0.9 times $D_2$. The third part is between the first part and the second part, so to form a recession. Therefore, when the microprobe 42 is inserted into the skin, it will be locked by the part of the skin that contacts the recession. It is noted that if the $D_3$ is less than 0.5 times $D_2$, the probe body 34 will break easily.

The probe body 34 is formed by selectively removing the base 11 by, e.g., etching. The main portion 341 is of a shape of cylinder, and the tip portion 342 is in a shape of a needle. The first isolation layer 36 is disposed on the probe bodies 34 and the backside surface 112 of the base 11 by physical vapor deposition (PVD). In this embodiment, the material of the first isolation layer 36 is Parylene, and the surface of the whole first isolation layer 36 is continuously disposed on the probe bodies 34 along the main portion 341 and the tip portion 342. The conductive layer 38 is plated on the first isolation layer 36, and the material of the conductive layer 38 is platinum (Pt). The material of platinum is not harmful to health and is safe to penetrate through the stratum corneum into the stratum germinativum. The second isolation layer 40 is formed on the conductive layer 38 by physical vapor deposition (PVD). In this embodiment, the material of the second isolation layer 40 is Parylene (which is the same as the first isolation layer 36). The second isolation layer 40 has an opening 401 to expose the part of the conductive layer 38 on the tip portion 342.

Figure 3:
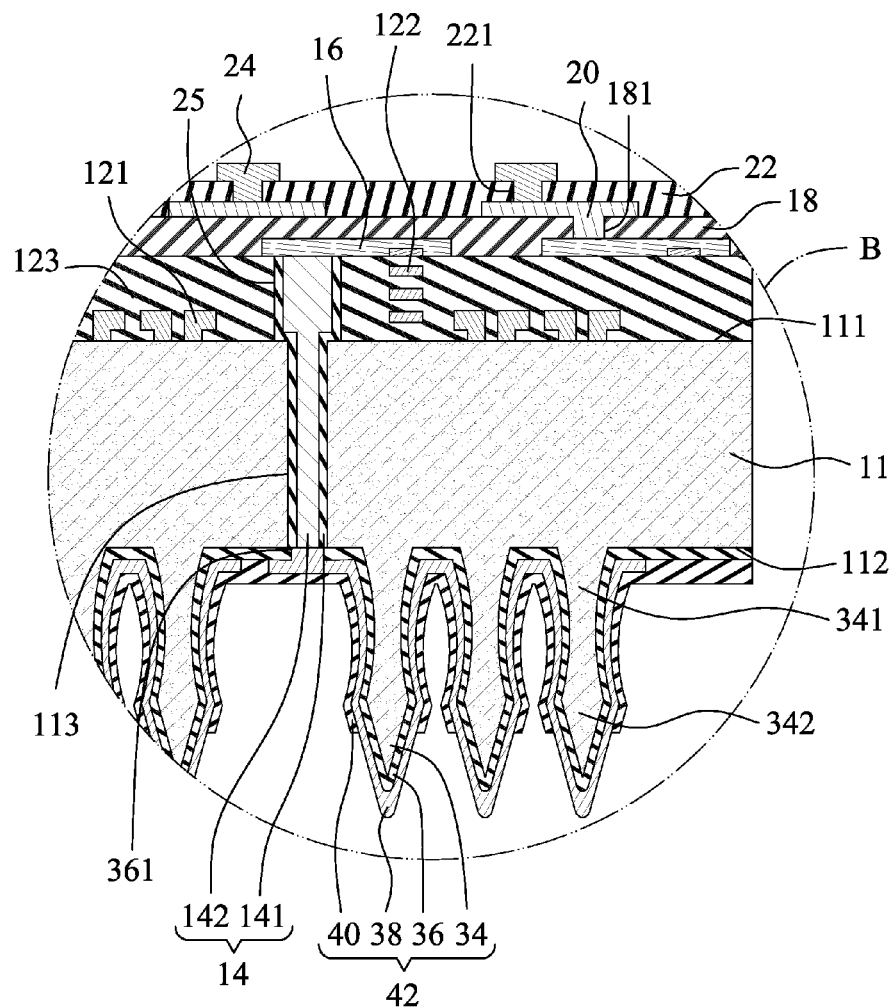
FIG. 3 illustrates a partially enlarged view of area B of FIG. 1.

Referring to FIG. 3, a partially enlarged view of area B of FIG. 1 is illustrated. The through silicon via 14 is disposed in the base hole 113, and penetrates through the base 11 and the integrated circuit portion 12. In this embodiment, the through silicon via 14 has a circular insulation material 141 and an interconnection metal 142. The circular insulation material 141 is disposed on the sidewall of the base hole 113 and the side wall of the upper blind hole 125, and defines a central groove. The interconnection metal 142 is disposed in the central groove, and the bottom end of the interconnection metal 142 is exposed from the backside surface 112 of the base 11 for electrical connection. The first isolation layer 36 has an opening 361 to expose the interconnection metal 142. The conductive layer 38 is formed on the first isolation layer 36 and also formed in the opening 361, so as to contact the interconnection metal 142. Thus, the conductive layer 38 is electrically connected to the through silicon via 14. As is well known, the signals from the human body, e.g., brain waves are low-frequency analog signals which are relatively weak. However, the signals of brain waves collected by the microprobe 42 can be transmitted to the integrated circuit portion 12 by the through silicon via 14, and then the electrical elements 121 will amplify the analog signals, and convert the amplified analog signals into digital signals. In order to ensure the signal transmission quality, the transmission path must be shortest to avoid noise interference.

In this embodiment, the through silicon via 14 can accomplish the above function, because the through silicon via 14 is disposed in each of the areas including the microprobes 42, so that signals collected by the microprobes 42 in the same area can be transmitted to the active surface 111 of the base 11 to operation by the shortest transmission path.

Figure 4:
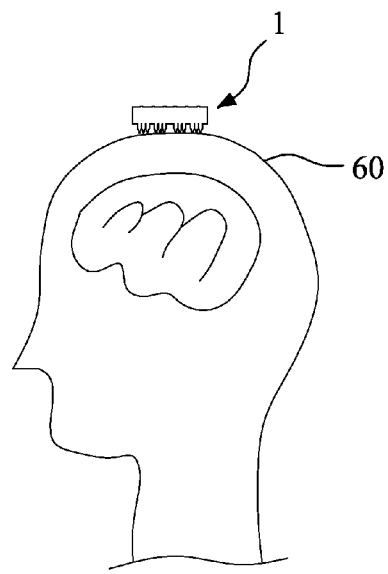
FIG. 4 illustrates the neural sensing device being used according to an embodiment of the present invention.

Referring to FIG. 4, an operation of the neural sensing device according to an embodiment of the present invention is illustrated. The neural sensing device 1 can be applied to a human scalp to collect the signals from human head 60, e.g., brain waves. Since the size of the neural sensing device 1 is very small, the neural sensing device 1 can move with a human body so that it is portable. In addition, the neural sensing device 1 can collect the signals from human head 60 by direct contact, thus, brain surgery is unnecessary.

Figure 4A:
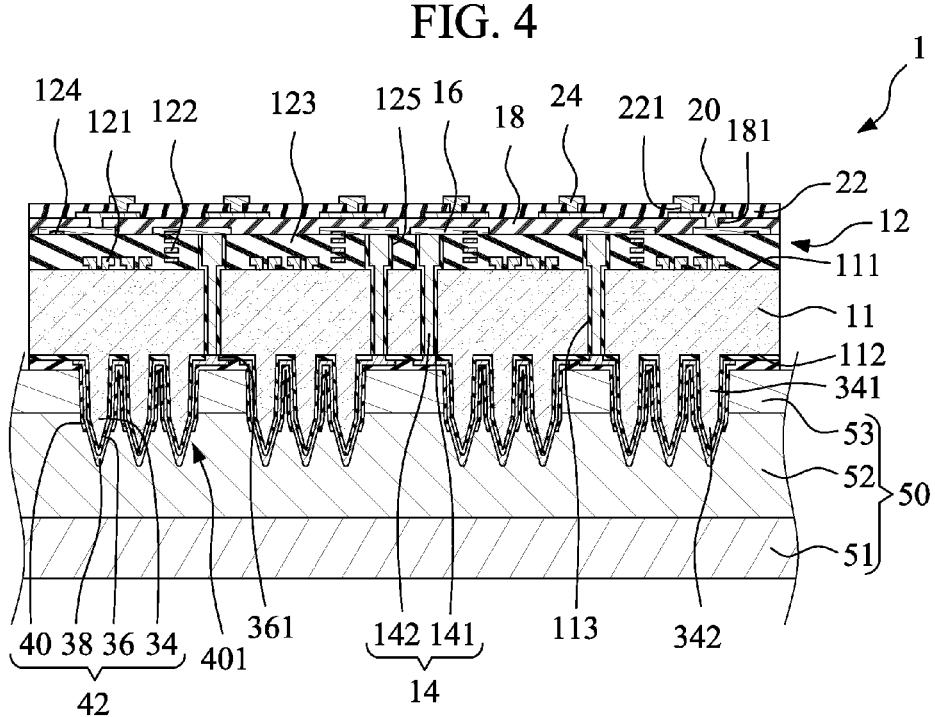
FIG. 4A illustrates an enlarged view of FIG. 4.

Referring to FIG. 4A, an enlarged view of FIG. 4 is illustrated. In order to collect the signals in the human body, the microprobes 42 of the neural sensing device 1 are inserted into the skin 50. As is well known, the skin 50 includes a dermis 51, a stratum germinativum (SG) 52 and a stratum corneum (SC) 53. Therefore, if the bio-signals in the stratum germinativum (SG) 52 are desired, the microprobes 42 must penetrate through the stratum corneum (SC) 53 and extend into the stratum germinativum (SG) 52 to collect the bio-signals. Since the conductive layer 38 corresponding to the stratum corneum (SC) 53 is covered by the second isolation layer 40, the measured result will not be affected by the undesired noises in the stratum corneum (SC) 53. Furthermore, the bottom of the neural sensing device 1 is also covered by the second isolation layer 40, the measured result will not be affected by the undesired noises from the surface of the skin 50, either. That is, only the exposed tip portion of the conductive layer 38 in the stratum germinativum (SG) 52 can collect the bio-signals. In addition, the length of the exposed tip portion of the conductive layer 38 is about 30 to 70 μm, so as to ensure the integrity of the collected signals.

In order to avoid the noise from the stratum corneum (SC) 53, the exposed tip portion of the conductive layer 38 in the stratum germinativum (SG) 52 must reach to about 30 to 70 μm.

The neural sensing device 1 of the present invention can be used but is not limited to collect the following physiological signals with various frequency ranges: Electroencephalography (EEG) (0-100 Hz), Electrocorticography (ECoG) (0-200 Hz), Neural Spike (300-7 kHz), Electrocardiogram (ECG) (0.05-1 kHz), Electromyogram (EMG) (0.01-10 kHz), and Electro-oculogram (EOG) (0-100 Hz). Thus, the neural sensing device 1 of the present invention can be used widely.

Figure 5:
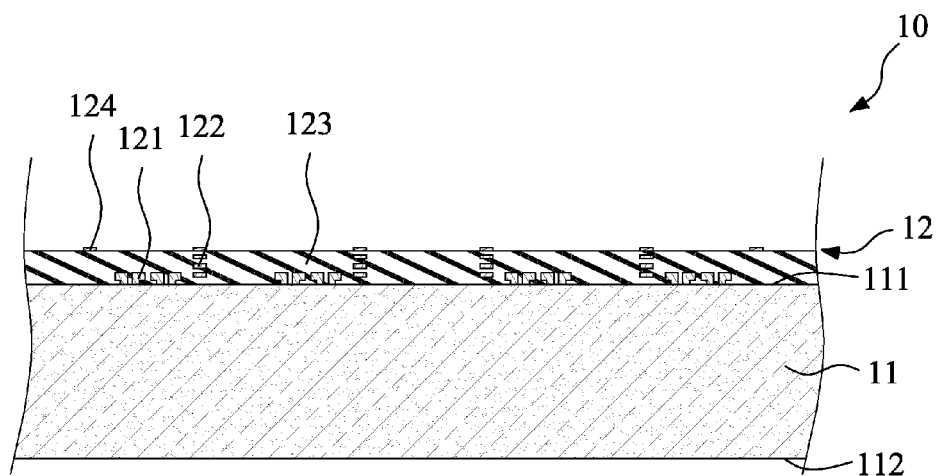
FIGS. 5 to 21 illustrate a method for making a neural sensing device according to an embodiment of the present invention.

Referring to FIGS. 5 to 21, a method for making a neural sensing device according to an embodiment of the present invention is illustrated. Referring to FIG. 5, a wafer 10 is provided. The wafer 10 has a base 11 and an integrated circuit portion 12. In this embodiment, the material of the base 11 is silicon, and the base 11 has an active surface 111 and a backside surface 112. The integrated circuit portion 12 is disposed on the active surface 111 of the base 11. In this embodiment, the integrated circuit portion 12 comprises a plurality of electrical elements 121, a plurality of metal layers 122, at least one dielectric layer 123 and at least one pad 124. The electrical elements 121, such as complementary metal-oxide-semiconductor (CMOS) micro-electro-mechanical systems (MEMS), simulators, controllers, RF telemetry, power receiving coil or an antenna, are disposed adjacent to the active surface 111 of the base 11 and covered by the dielectric layer 123. The metal layers 122 are covered by, and embedded in. the dielectric layer 123. The pad 124 and the upmost layer of the metal layers 122 are not covered by the dielectric layer 123. In this embodiment, the thickness of the base 11 is about 350 μm and the thickness of the integrated circuit portion 12 is about 18 μm.

Figure 6:
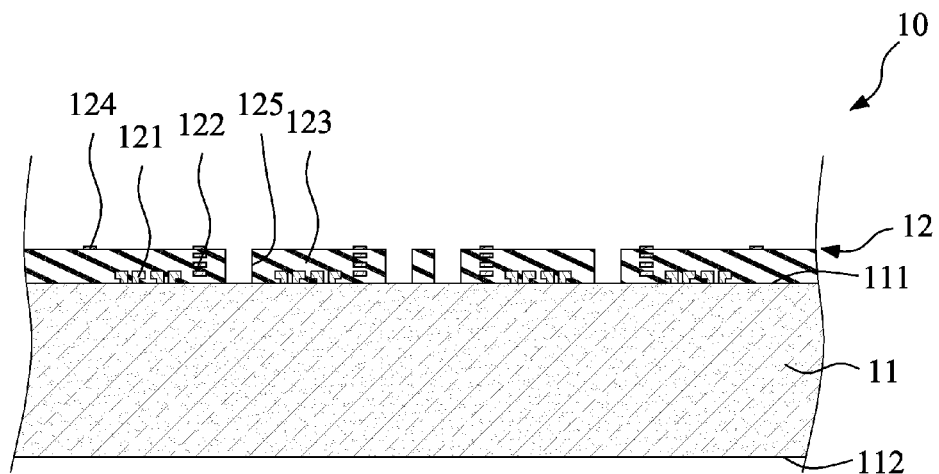

Referring to FIG. 6, at least one upper blind hole 125 is formed to penetrate through the integrated circuit portion 12 and expose a part of the active surface 111 of the base 11.

Figure 7:
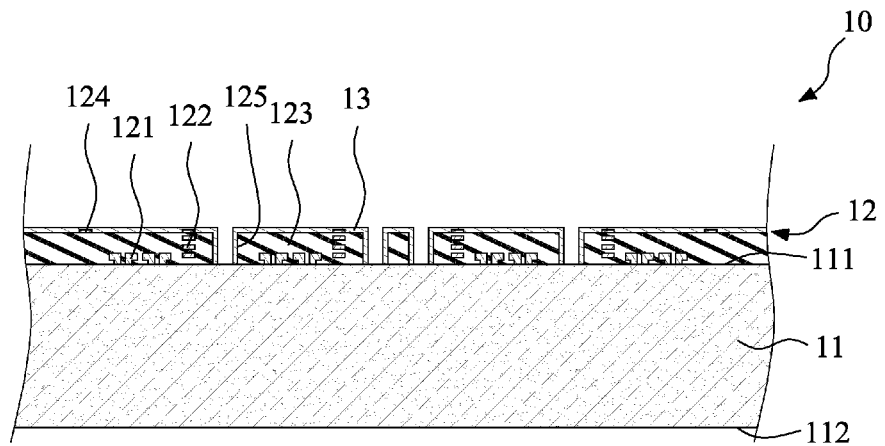

Referring to FIG. 7, a photoresist layer 13 is formed on the integrated circuit portion 12 and the sidewall of the upper blind hole 125. Then, the photoresist layer 13 that is disposed at the bottom of the upper blind hole 125 is removed so that the part of the active surface 111 of the base 11 is exposed.

Figure 8:
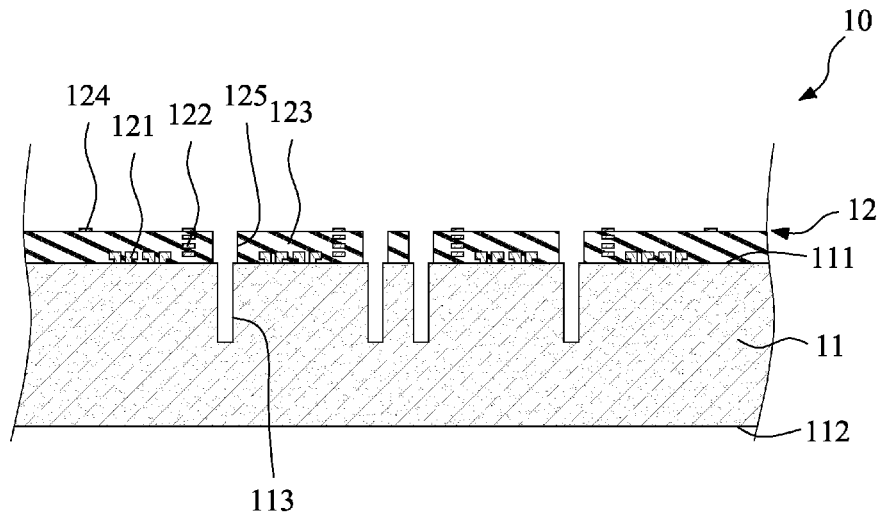

Referring to FIG. 8, at least one base hole 113 is formed on the exposed part of the active surface 111 of the base 11 by, for example, dry etching. In this embodiment, the base hole 113 is a blind hole that does not penetrate through the base 11. The base hole 113 is communicated with the upper blind hole 125, and the diameter of the base hole 113 is smaller than that of the upper blind hole 125. In this embodiment, the depth of the base hole 113 is about 200 μm, and the diameter of the base hole 113 is about 30 μm. Then, the photoresist layer 13 is released.

Figure 9:
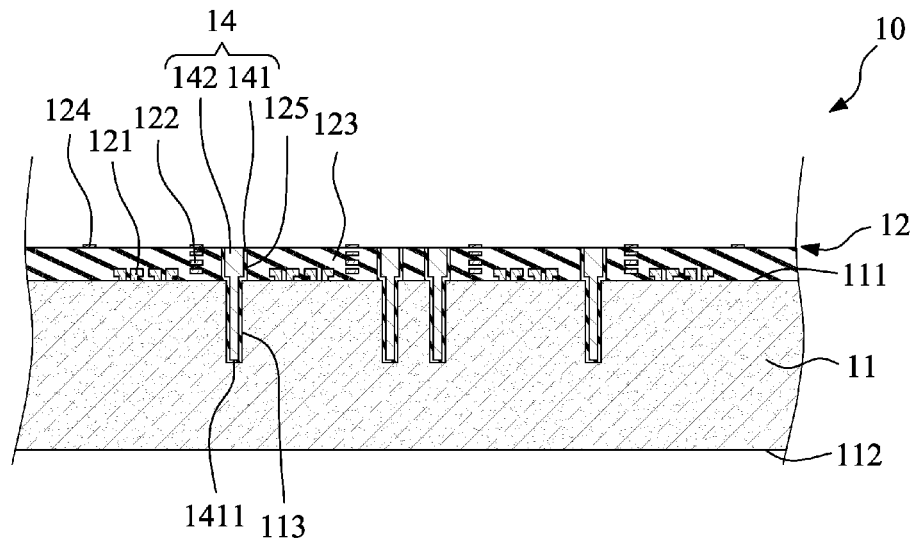

Referring to FIG. 9, a circular insulation material 141 is formed on the sidewall of the upper blind hole 125 and the sidewall of the base hole 113 so as to define a central groove. The circular insulation material 141 has a bottom portion 1411. Then, an interconnection metal 142 fills in the central groove so as to form a through silicon via 14. In this embodiment, the material of the circular insulation material 141 is $SiO_x$, and the material of the interconnection metal 142 is Cu.

Figure 10:
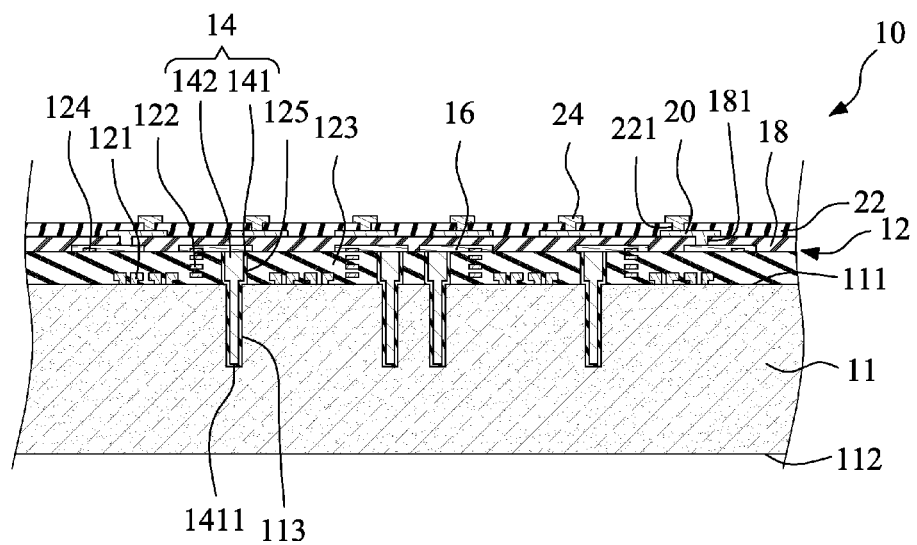

Referring to FIG. 10, a first redistribution layer 16 is formed on the integrated circuit portion 12 to electrically connect the pad 124, the upmost layer of the metal layers 122 and the through silicon via 14. Then, a first protection layer 18 is formed on the integrated circuit portion 12 to cover the first redistribution layer 16, wherein the first protection layer 18 has at least one opening 181 to expose a part of the first redistribution layer 16. Then, a second redistribution layer 20 is formed on the first protection layer 18 and the in opening 181 to electrically connect the first redistribution layer 16. Then, a second protection layer 22 is formed on the first protection layer 18 to cover the second redistribution layer 20, wherein the second protection layer 22 has at least one opening 221 to expose a part of the second redistribution layer 20. Then, at least one under bump metallurgy (UBM) 24 is formed on the second protection layer 22 and in the opening 221 to electrically connect the second redistribution layer 20.

Figure 11:
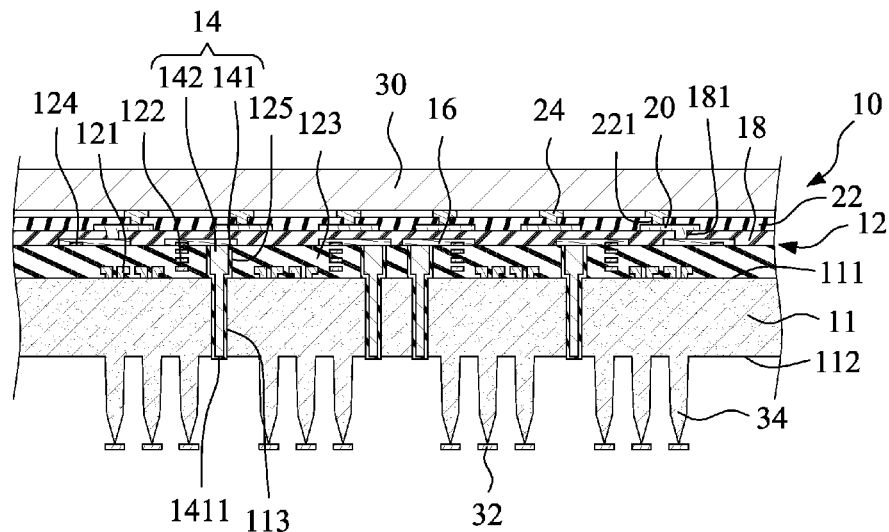

Referring to FIG. 11, the wafer 10 is attached to a carrier 30, wherein the under bump metallurgy (UBM) 24 contacts the carrier 30. Then, a hard mask 32 is applied to the backside surface 112 of the base 11. The hard mask 32 has a pattern so that a part of the backside surface 112 of the base 11 is exposed. Then, the base 11 is selectively removed from the backside surface 112 by, for example, etching That is, the exposed part of the backside surface 112 that is not covered by the hard mask 32 is removed by, for example, etching Therefore, a plurality of needle-like probe bodies 34 are formed from the base 11 and protrudes from the backside surface 112 of the base 11. The removal process proceeds until the bottom portion 1411 of the circular insulation material 141 of the through silicon via 14 is exposed. Meanwhile, the base hole 113 of the base 11 becomes a through hole. In this embodiment, the height of the probe body 34 is about 150 μm, and the thickness of the remaining base 11 is about 200 μm.

Figure 12:
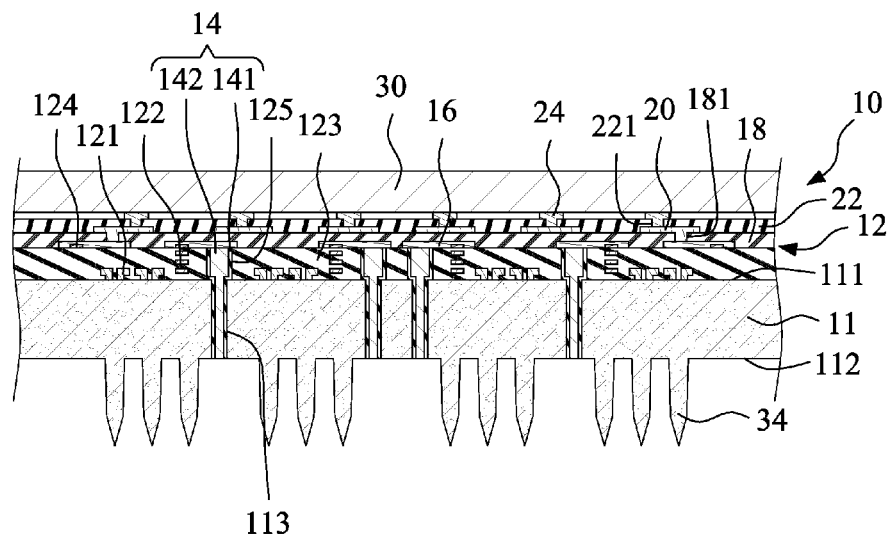

Referring to FIG. 12, the hard mask 32 is released. Then, the bottom portion 1411 of the circular insulation material 141 of the through silicon via 14 is removed so that the interconnection metal 142 is exposed from the backside surface 112 of the base 11.

Figure 13:
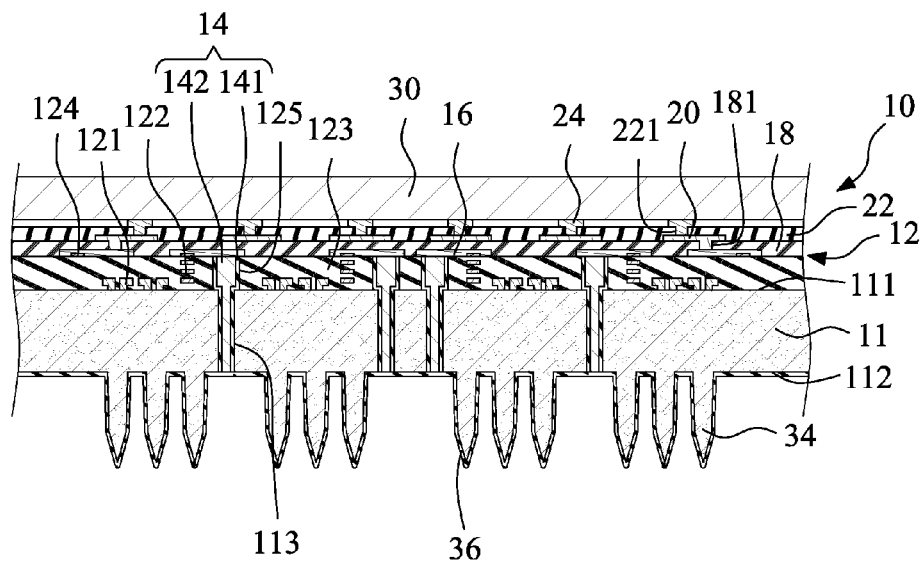

Referring to FIG. 13, a first isolation layer 36 is formed on the probe bodies 34 and the backside surface 112 of the base 11 by physical vapor deposition (PVD). In this embodiment, the material of the first isolation layer 36 is Parylene, and the thickness of the whole first isolation layer 36 is even. In this embodiment, the thickness of the first isolation layer 36 is about 1 to 2 μm. In order to make the first isolation layer 36 has an even thickness; the processing condition is described as follows. The viscosity of the Parylene solution is determined that the ratio of the weight of Parylene to the weight of solvent is 1:1. The spray speed may be 40, 50, 60 rpm. The spraying step is repeated four or five times to form the isolation layer 36 having the proper thickness.

Figure 14:
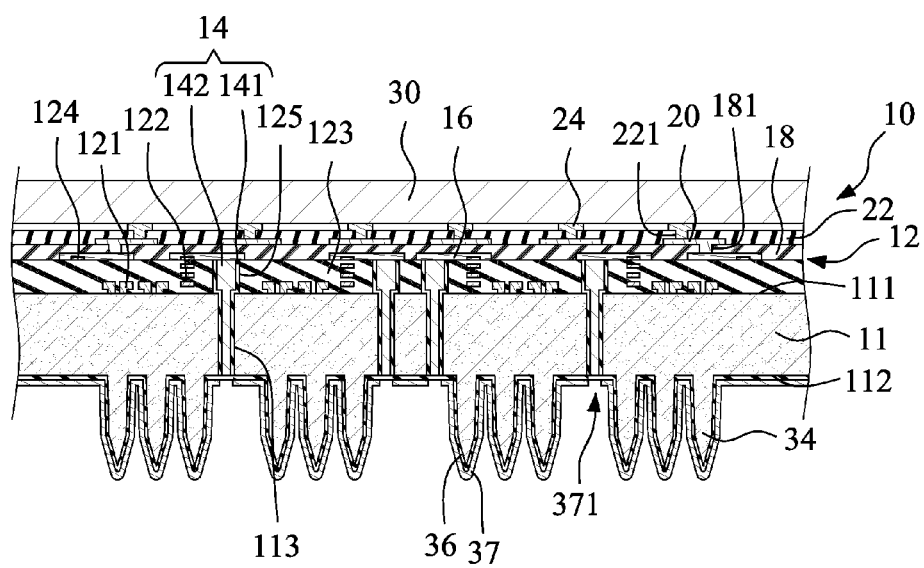

Referring to FIG. 14, a photoresist layer 37 is formed on the first isolation layer 36. The photoresist layer 37 has at least one opening 371 corresponding to the through silicon via 14 so that a part of the first isolation layer 36 is exposed. In this embodiment, the thickness of the photoresist layer 37 is about 3 to 5 μm, and the diameter of the opening 371 is about 20 μm.

Figure 15:
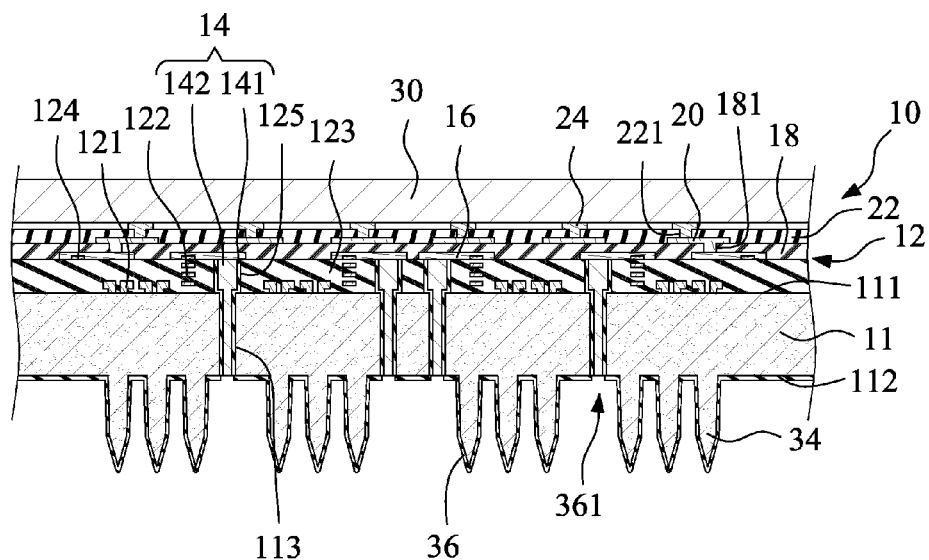

Referring to FIG. 15, the exposed part of the first isolation layer 36 that is not covered by the photoresist layer 37 is removed by, for example, reactive ion etching (RIE). Therefore, the first isolation layer 36 has an opening 361 to expose the interconnection metal 142 of the through silicon via 14. Then, the photoresist layer 37 is released.

Figure 16:
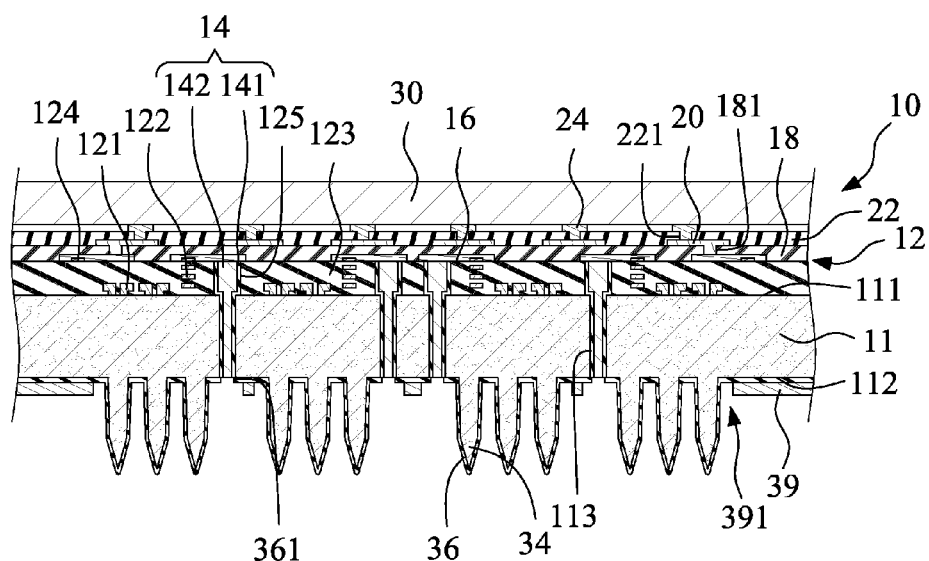

Referring to FIG. 16, a photoresist layer 39 is formed on the first isolation layer 36. The photoresist layer 39 has at least one opening 391 to expose the interconnection metal 142 of the through silicon via 14 and the first isolation layer 36 disposed on the probe bodies 34.

Figure 17:
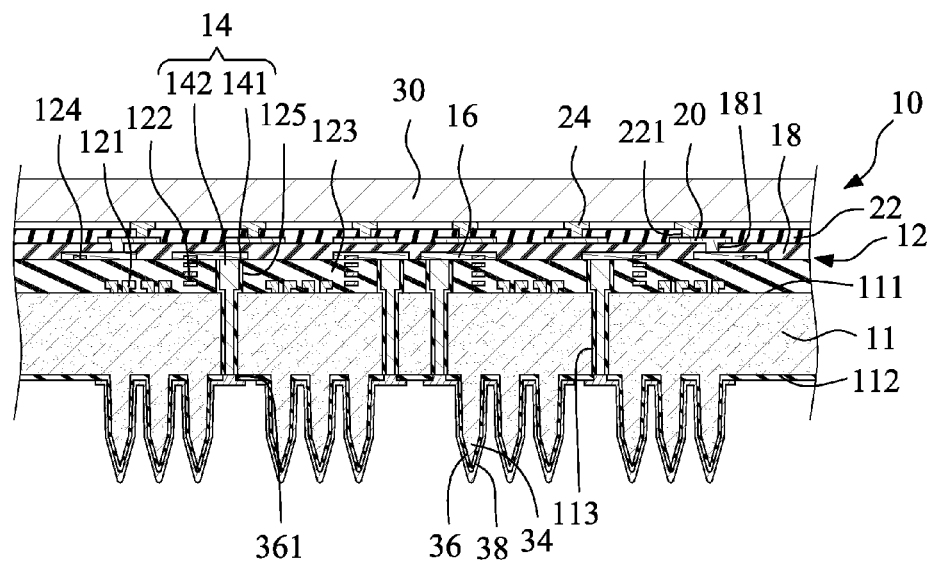

Referring to FIG. 17, a conductive layer 38 is formed in the opening 391 of the photoresist layer 39 by plating. Therefore, the conductive layer 38 is formed on the first isolation layer 36 disposed on the probe bodies 34 and also formed on the interconnection metal 142 of the through silicon via 14, so as to contact the interconnection metal 142 of the through silicon via 14. In this embodiment, the material of the conductive layer 38 is platinum, and the thickness of the conductive layer 38 is about 450 nm. Then, the photoresist layer 39 is released, and a part of the first isolation layer 36 is exposed.

Figure 18:
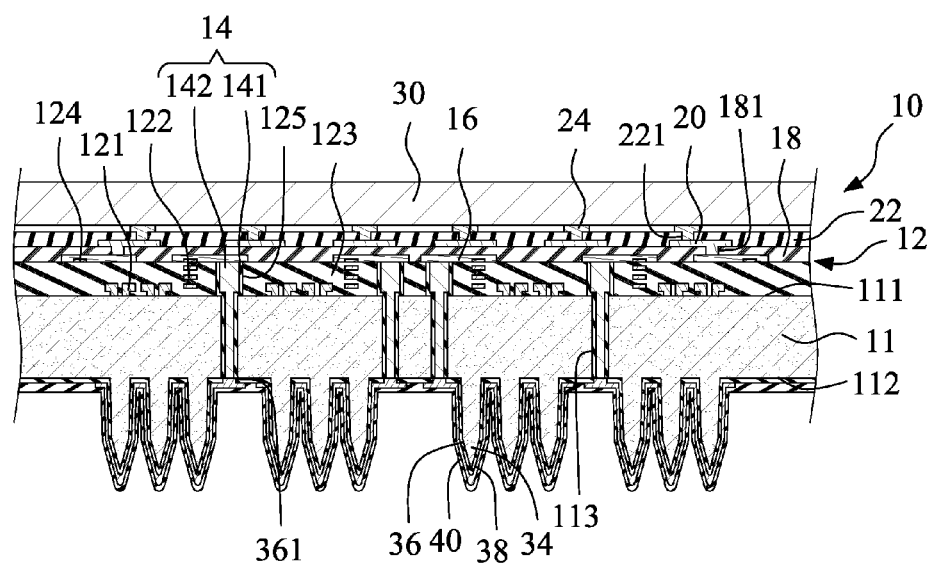

Referring to FIG. 18, a second isolation layer 40 is formed on the conductive layer 38 and the exposed part of the first isolation layer 36 by physical vapor deposition (PVD). In this embodiment, the material of the second isolation layer 40 is Parylene which is the same as the first isolation layer 36, and the thickness of the second isolation layer 40 is about 1 to 2 μm which is the same as the first isolation layer 36. The processing condition of the second isolation layer 40 is the same as the first isolation layer 36. However, the material and the thickness of the second isolation layer 40 may be different from that of the first isolation layer 36.

Figure 19:
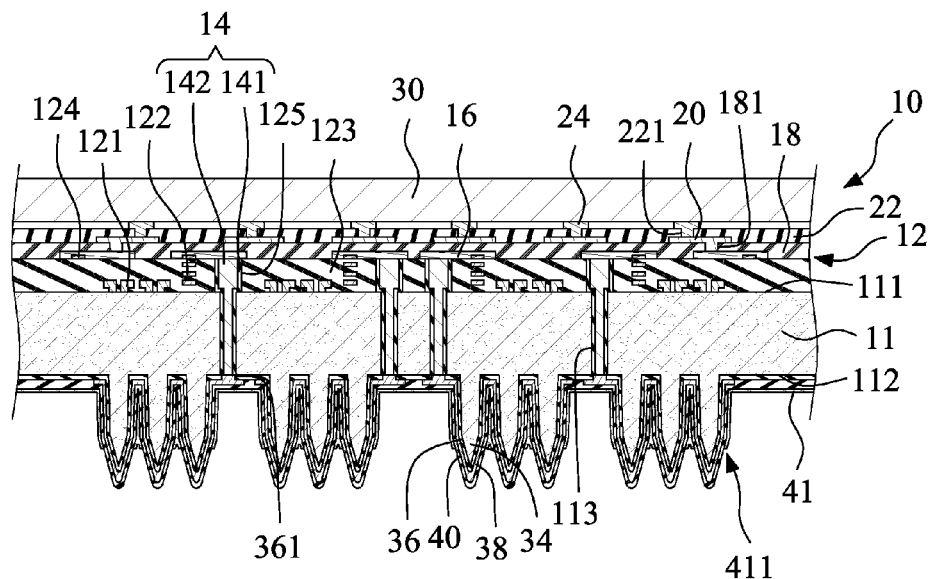

Referring to FIG. 19, a photoresist layer 41 is formed on the second isolation layer 40. The photoresist layer 41 has at least one opening 411 to expose the tip of the probe body 34. In this embodiment, the thickness of the photoresist layer 41 is about 3 to 5 μm, and the width of the opening 411 is about 50 μm.

Figure 20:
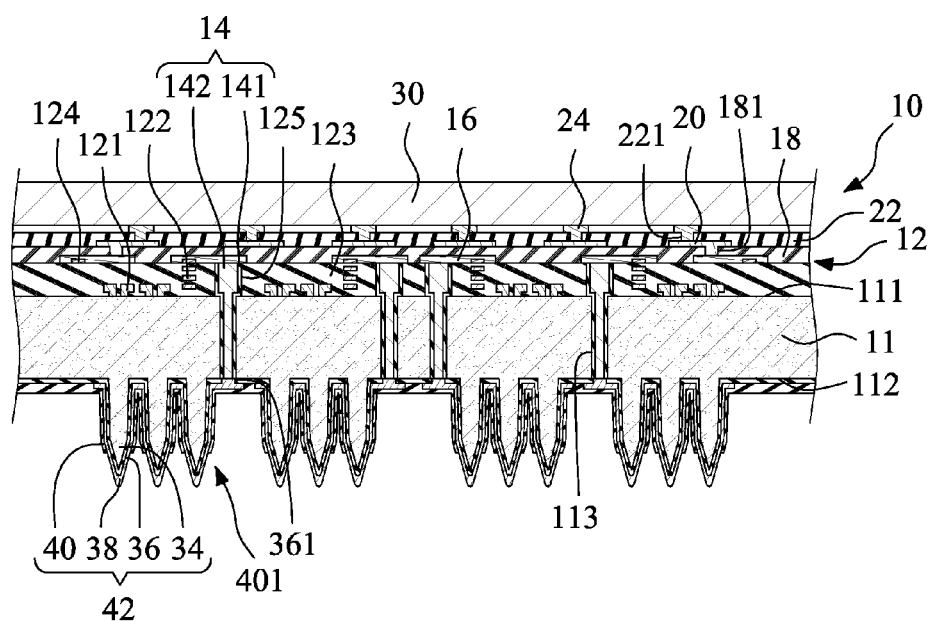

Referring to FIG. 20, the exposed part of the second isolation layer 40 that is not covered by the photoresist layer 41 is removed by, for example, reactive ion etching (RIE). Therefore, the second isolation layer 40 has at least one opening 401 to expose a part (i.e., the tip) of the conductive layer 38. Then, the photoresist layer 41 is released, and the microprobes 42 are formed.

Figure 21:
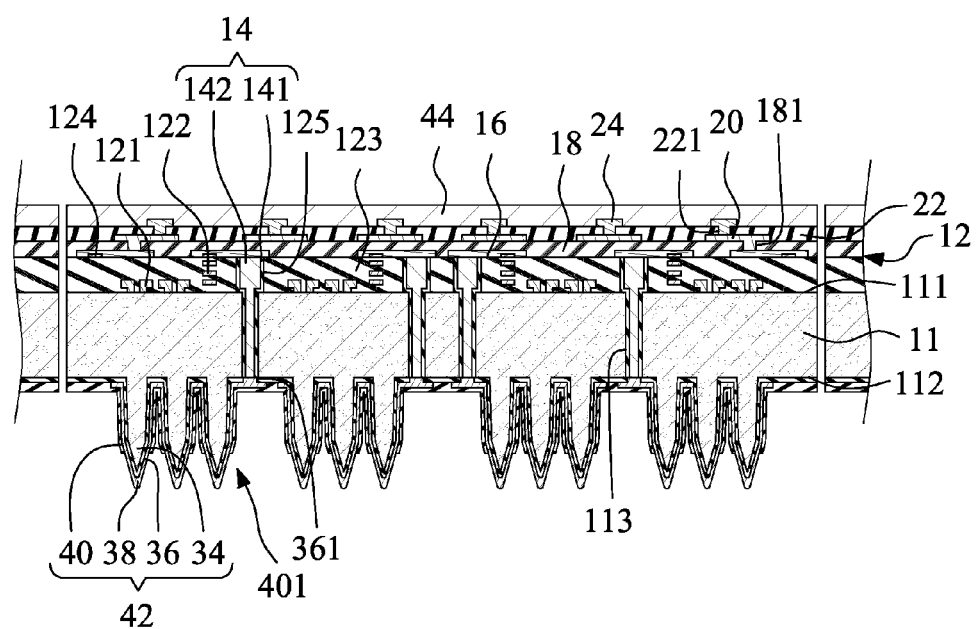

Referring to FIG. 21, the wafer 10 is released from the carrier 30, and then attached to a dicing tape 44. Then, the wafer 10 and the dicing tape 44 are diced. Then, the dicing tapes 44 are stripped so as to form a plurality of neural sensing devices 1 as shown in FIG. 1.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily be drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A neural sensing device, comprising:
   a base having an active surface and a backside surface;
   an integrated circuit portion disposed on the active surface of the base; and
   a plurality of microprobes disposed on the backside surface of the base, each of the microprobes comprising:
   a probe body protruding from the backside surface of the base and including a tip at a distal end;

a first isolation layer covering the probe body;
a conductive layer covering the first isolation layer and electrically connected to the integrated circuit portion; and
a second isolation layer covering the conductive layer and having an opening to expose the conductive layer around a portion of the tip.

2. The neural sensing device of claim 1, further comprising a conductive via disposed in the base and electrically connected to the integrated circuit portion and the conductive layer.

3. The neural sensing device of claim 1, wherein the integrated circuit portion comprises a plurality of electrical elements, a plurality of metal layers and at least one dielectric layer, the electrical elements disposed adjacent to the active surface of the base and covered by the dielectric layer, and the metal layers embedded in the dielectric layer.

4. The neural sensing device of claim 1, wherein the probe body of each of the microprobes is formed from the base.

5. The neural sensing device of claim 1, wherein the material of the base and the probe body is the same.

6. The neural sensing device of claim 1, wherein the materials of the first isolation layer and the second isolation layer are insulative.

7. The neural sensing device of claim 1, wherein the exposed portion of the conductive layer around the tip is about 30 to 70 μm in length.

8. The neural sensing device of claim 1, further comprising:
at least one redistribution layer disposed on and electrically connected to the integrated circuit portion;
at least one protection layer covering the redistribution layer; and
at least one under bump metallurgy (UBM) disposed on the protection layer and electrically connected to the redistribution layer.

9. The neural sensing device of claim 1, wherein the probe body of each of the microprobes has a main portion and the tip, the main portion connected to the base and the tip, the diameter of the portion of the main portion connected to the base having a diameter greater than the portion of the main portion connected to the tip.

10. The neural sensing device of claim 2, wherein the conductive via is a through silicon via.

11. The neural sensing device of claim 10, wherein the base has at least one base hole, the through silicon via is disposed in the base hole and has a circular insulation material and an interconnection metal, the circular insulation material is disposed on a sidewall of the base hole and defines a central groove, and the interconnection metal is disposed in the central groove.

12. The neural sensing device of claim 10, wherein the through silicon via further penetrates through the integrated circuit portion.

13. A neural sensing device, comprising:
a base;
an integrated circuit portion disposed on an active surface of the base;
a plurality of microprobes protruding from a backside surface of the base, each of the microprobes having a probe body made of the same material as the base and covered by a first isolation layer, wherein a conductive layer covers the first isolation layer and is covered by a second isolation layer except for a portion of a tip of the microprobe; and
at least one through silicon via disposed in the base and electrically connecting the integrated circuit portion and the microprobes.

14. The neural sensing device of claim 13, wherein the base has at least one base hole, the through silicon via is disposed in the base hole and has a circular insulation material and an interconnection metal, the circular insulation material is disposed on a sidewall of the base hole and defines a central groove, and the interconnection metal is disposed in the central groove.

15. The neural sensing device of claim 13, wherein the through silicon via further penetrates through the integrated circuit portion.

16. The neural sensing device of claim 13, further comprising:
at least one redistribution layer disposed on and electrically connected to the integrated circuit portion and the conductive via;
at least one protection layer covering the redistribution layer; and
at least one under bump metallurgy (UBM) disposed on the protection layer and electrically connected to the redistribution layer.

17. The neural sensing device of claim 13, wherein the exposed portion of the conductive layer around the tip of the microprobe is about 30 to 70 μm in length.

18. The neural sensing device of claim 13, wherein the integrated circuit portion comprises a plurality of electrical elements, a plurality of metal layers and at least one dielectric layer, the electrical elements disposed adjacent to the active surface of the base and covered by the dielectric layer, and the metal layers embedded in the dielectric layer.

19. The neural sensing device of claim 13, wherein the materials of the first isolation layer and the second isolation layer are insulative.

* * * * *